United States Patent
Nyfors

(10) Patent No.: US 8,570,050 B2
(45) Date of Patent: Oct. 29, 2013

(54) FLOW MEASUREMENTS

(75) Inventor: Ebbe Gustaf Nyfors, Sandnes (NO)

(73) Assignee: Roxar Flow Measurements AS, Bergen (NO)

( * ) Notice: Subject to any disclaimer, the term of this patent is extended or adjusted under 35 U.S.C. 154(b) by 906 days.

(21) Appl. No.: 12/522,961

(22) PCT Filed: Jan. 11, 2008

(86) PCT No.: PCT/NO2008/000013
§ 371 (c)(1),
(2), (4) Date: Jan. 12, 2010

(87) PCT Pub. No.: WO2008/085065
PCT Pub. Date: Jul. 17, 2008

(65) Prior Publication Data
US 2010/0145636 A1    Jun. 10, 2010

(30) Foreign Application Priority Data
Jan. 12, 2007    (NO) .................................. 20070231

(51) Int. Cl.
*G01R 27/04* (2006.01)
*G01N 22/04* (2006.01)

(52) U.S. Cl.
CPC ..................................... *G01N 22/04* (2013.01)
USPC ...................................................... 324/634

(58) Field of Classification Search
None
See application file for complete search history.

(56) References Cited

U.S. PATENT DOCUMENTS

| 4,203,067 | A | * | 5/1980 | Fitzky et al. | 324/636 |
| 4,888,547 | A | | 12/1989 | McGinn et al. | |
| 5,397,993 | A | * | 3/1995 | Tews et al. | 324/634 |
| 5,826,458 | A | * | 10/1998 | Little | 73/73 |
| 6,826,964 | B2 | * | 12/2004 | Nyfors | 73/861.04 |
| 6,915,707 | B2 | | 7/2005 | Nyfors et al. | |
| 6,922,061 | B2 | * | 7/2005 | Herrmann et al. | 324/633 |
| 7,223,608 | B2 | * | 5/2007 | Gopalsami et al. | 436/149 |

FOREIGN PATENT DOCUMENTS

| DE | 44 11 815 | 10/1995 |
| GB | 2 194 058 | 2/1988 |
| WO | WO 95/27895 | 10/1995 |
| WO | WO 01/88513 | 11/2001 |
| WO | WO 03/034051 | 4/2003 |

OTHER PUBLICATIONS

International Search Report for PCT/N02008/000013, mailed May 7, 2008.

(Continued)

*Primary Examiner* — Paresh Patel
(74) *Attorney, Agent, or Firm* — Nixon & Vanderhye P.C.

(57) ABSTRACT

This invention relates to a measuring instrument for measurement of a flow (1) comprising—a dielectric resonator sensor (3) arranged in a pipeline (2), said resonator (3) having a surface (4) facing a flow volume, —a sensor drive unit (12) being coupled to said sensor (3) and which is adapted to provide a driving or excitation signal to said sensor (3) resulting in the excitation of an electromagnetic resonance in said sensor causing a fringing electromagnetic field (5) adjacent to said surface (4) facing said wet gas flow (1), —a recording unit (10) coupled to said sensor (3) and which is adapted to measure a resonance property of said sensor (3) while said wet gas flow (1) moves past said sensor surface (4), and—a processing unit (11) which is adapted to estimate a property of at least a part of said wet gas flow (1).

19 Claims, 10 Drawing Sheets

(56) References Cited

OTHER PUBLICATIONS

International Preliminary Report on Patentability for PCT/N02008/000013, mailed May 7, 2008.

Norwegian Search Report for Norway Application No. 2007 0231, dated Jul. 24, 2007.

* cited by examiner

FLOW MEASUREMENTS

This application is the U.S. national phase of International Application No. PCT/NO2008/000013 filed 11 Jan. 2008, which designated the U.S. and claims priority to Norway Application No. 20070231 filed 12 Jan. 2007, the entire contents of each of which are hereby incorporated by reference.

FIELD OF THE INVENTION

The present invention relates in general to measurements of fluid flow in a pipeline.

More specifically the present invention relates to measurement of water volume fraction (WVF), liquid film thickness, liquid film flow speed and/or salinity in a fluid flow, particularly in a wet gas or multiphase flow in a pipeline for transporting hydrocarbon-containing fluids, which in many cases additionally contains water, salt or other substances occurring in the exploration of oil and gas reservoirs.

BACKGROUND TO THE INVENTION AND PRIOR ART

A number of different commercial flow meters are available on the market for the measurement of the water content of oil. Some meters are based on the use of radioactive radiation, some are capacitive, and some are based on the use of microwaves.

Microwave sensors are attractive because they are not limited by the health risks associated with radioactive radiation based meters and their fairly low accuracy or the undesirable influence of contamination on the capacitive sensors.

An example of a method for measuring properties of flowing fluids and a metering device and a sensor used for performing this method has been described in International Patent Application PCT/NO01/00200, for which a US-patent has been granted (U.S. Pat. No. 6,826,964 B2). The sensor uses the microwave resonance principle for the measurement of oil-continuous fluids (water drops and gas bubbles in oil, i.e. the oil is a continuous phase) and the measurement of conductivity for water-continuous fluids (oil drops and gas bubbles in water, i.e. the water is the continuous phase, and is intended for installation at a production zone inside an oil well.

Another example of a method for measuring flowing fluids with a far higher gas content, i.e. wet gas (a wet gas flow is a multiphase flow with a high gas volume fraction, usually called the gas void fraction (GVF), typically >99%) or high-gas multiphase flow, has been described in U.S. Pat. No. 6,915,707. This is also based on the microwave resonance principle.

The microwave resonance principle is based on measuring the permittivity/dielectric constant of the flow. Because the permittivity of water is high (in the order of 80) compared to that of oil (in the order of 1.5-3) or gas (even lower than for oil) the permittivity of a mixture of these three constituents is dominated by the contribution from water. Methods based on measuring the permittivity (microwave and capacitive methods) therefore provide the highest sensitivity for measuring the WVF of a mixture. Because microwave resonators are inherently stabile and the resonant frequency and quality factor (Q-factor), which are the two measurable properties of a resonance, can be measured with a high accuracy, the microwave resonance method is the most sensitive and accurate method available for measuring the WVF of a wet gas flow. However, when the WVF becomes very low, the permittivity of the mixture (i.e. the flowing fluid) starts to become dominated by the contributions from the oil and the gas. Especially the permittivity of the gas depends on the pressure and the temperature. To be able to resolve the contribution from the water one needs to know the contributions from the gas and the oil. E.g. the invention described in U.S. Pat. No. 6,915,707 also uses the hydrocarbon composition and measurements of temperature and pressure as inputs, and models for calculating the permittivity of the oil and the gas. The accuracy of the measurement of the WVF is then limited by the accuracy of the models, and the accuracy of the measurements of the temperature and pressure.

In a wet gas flow it is important to know the WVF because of the problems with hydrate formation, scaling, and corrosion caused by the water. Also the salinity of the water, caused by the production of formation water, is a very important factor as it strongly affects both corrosion and the formation of scale. As described above, present measurement solutions have limitations in the low end of WVF, while the known problems of hydrate formation and corrosion are still significant. Although at low WVF it will take more time for the smaller amount of water (possibly formation water) to cause deteriorating effects on the production flow, the problems are still highly relevant. Thus, it would be desirable to be able to improve the quantitative measurement of WVF in the flow, particularly at low water volume fractions, as the uncertainty of presently commercially available meters is limited at low values of WVF.

In this specification the Q-factor is defined as $2\pi$ multiplied with the stored energy/the loss in one oscillation period. Transferred to measurable variables this means that the Q-factor is obtained through the ratio between the resonance frequency and the peak width. The peak width is measured 3 dB beneath the top, i.e. the half effect width. According to a preferred embodiment of the invention both the Q-factor are measured, thus enabling the calculation of both the salinity and the water content.

The object of the invention is achieved by providing a method of measuring a wet gas flow in a pipeline according to the invention and a corresponding measuring instrument for performing the method according to the invention. More specifically the object of the invention is obtained as disclosed in the accompanying independent claims.

SHORT DESCRIPTION OF THE DRAWINGS

The invention is below described in further detail with references to the appended drawings, wherein FIG. 1 illustrates a dielectric resonator sensor of the measuring instrument according to the invention. It is shown mounted in the plane end of a metal cylinder as a stand-alone sensor e.g. for tests in a laboratory.

DETAILED DESCRIPTION OF THE INVENTION

Figure 1:
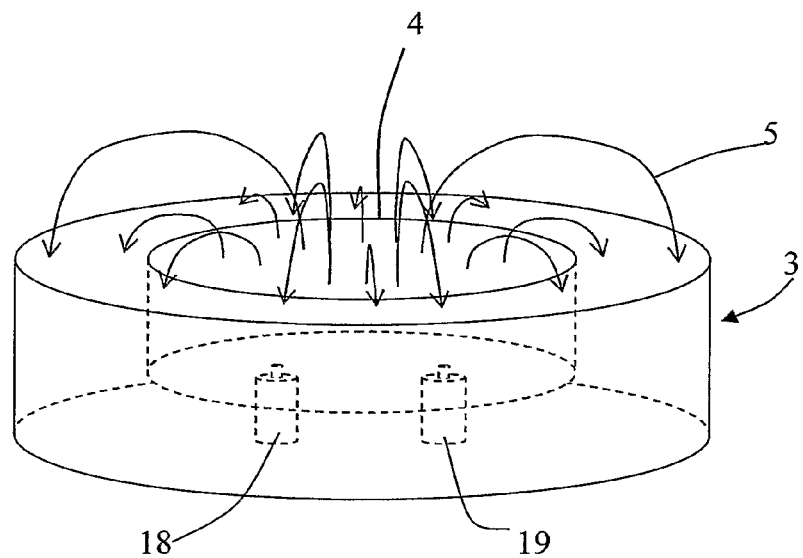

The measuring instrument according to the invention comprises a dielectric resonator sensor 3, as shown in FIG. 1, preferably having a substantially cylindrical shape, arranged so as to be able to excite a fringing field 5 by applying a varying voltage through one of the electrodes 18,19 that extends out from a surface 4 of said resonator sensor 3 and, and resulting resonance frequency being measured at one of the electrodes 18,19. The function of the sensor per se in known to a person skilled in the art. Now referring to FIG. 2 the field extends into a flow volume 1 inside a pipeline 2, said pipeline 2 being installed as part of a wet gas or multiphase flow conveying system, i.e. the flow volume normally contains a wet gas or multiphase flow 1. In the following description the word multiphase will be dropped for simplicity, and because the main application of the invention is to improve the accuracy of the measurement of WVF and/or salinity in the water of a wet gas flow at very low WVF. The invention is, however, not limited to very low WVF, i.e. it can be used with a general multiphase flow as a salinity or WVF sensor.

Figure 2:
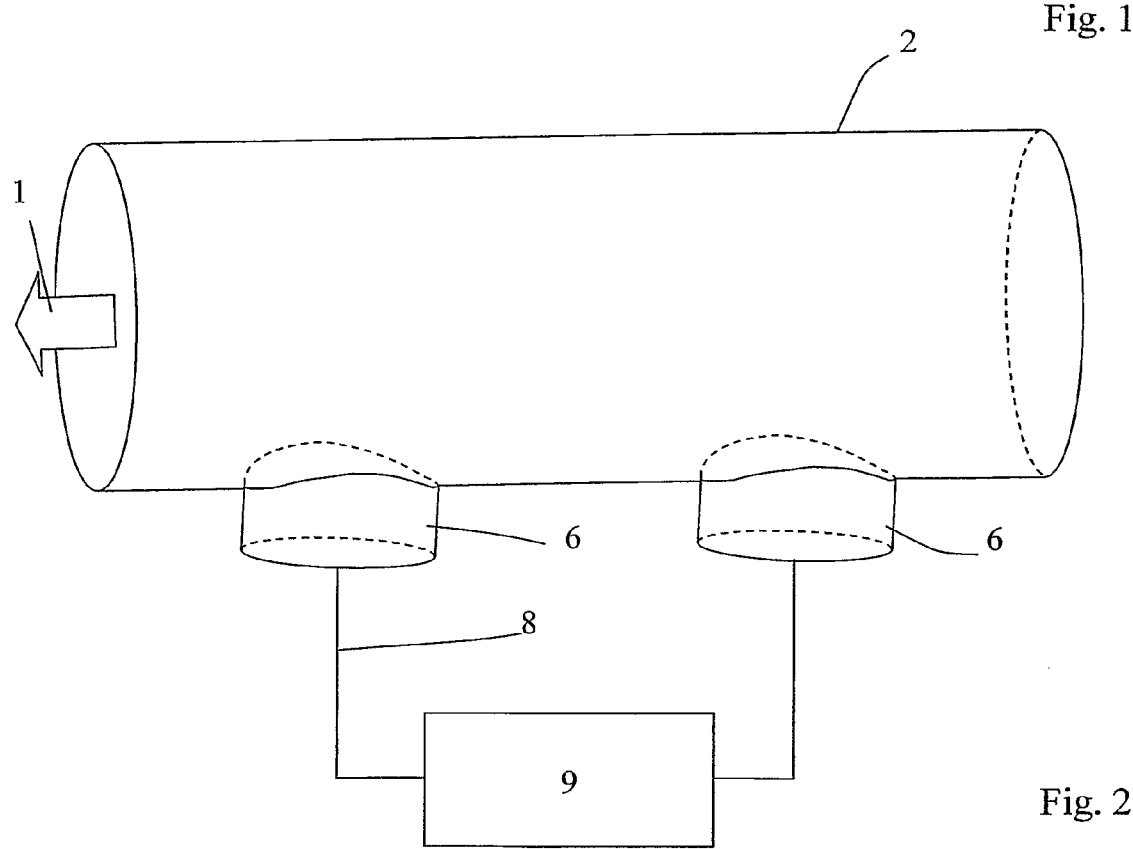
FIG. 2 illustrates the dielectric resonator sensor in the measuring instrument arranged in a pipeline for performing the method according to the invention. An assembly version with two sensors is shown.

FIG. 2 illustrates how the dielectric resonator sensor 3 is preferably mounted in a cavity 6 in said pipeline 2. The cavity 6 may have a shape similar to the shape of the dielectric resonator sensor 3. The cavity 6 is preferably defined by the wall of the pipeline 2, i.e. so that the resonator sensor 3 is at least partially enclosed by the metal walls of said cavity 6 in said pipeline 2. In a preferred embodiment of the measuring instrument according to the invention, the resonator sensor 3 is arranged so that an end surface 4 will be exposed to a wet gas flow 1 in said pipeline 2. Preferably, said end surface 4 is arranged so as to be substantially flush with a longitudinal wall inside the pipeline 2. The resonance mode of a cylindrically shaped dielectric resonator sensor having the lowest frequency will be the $TM_{01}$-mode, whose electromagnetic field is circularly symmetric. Because of the symmetry it will be virtually non-radiating, but it will have a fringing field 5 that extends out from said exposed surface 4 of the sensor 3.

The fringing field 5 decreases exponentially as a function of the distance from said sensor surface, i.e. the field strength is highest near said surface 4 of said sensor. Electric field lines of the fringing field 5 extend from said surface 4 of said sensor 3 to the metal wall of the pipeline surrounding said resonator sensor 3.

In another embodiment of the measuring instrument according to the invention the dielectric resonator sensor 3 may have a rectangular cross section, and be mounted in a correspondingly shaped cavity 6 in said pipeline. In this case the resonance mode is called the $TM_{11}$-mode.

Because the fringing field 5 of the resonator 3 penetrates into medium 1 in the volume outside the dielectric resonator, the fringing field 5 of the dielectric resonator sensor 3 is affected by medium 1. Thereby, the resonant frequency $f_r$ and the Q-factor of the resonator is also affected by the permittivity $\epsilon_r = \epsilon' - j\epsilon''$ of the medium in that volume. Due to the exponentially decreasing nature of the external electric field, the sensor is most sensitive to the medium closest to the sensor surface. The medium may be e.g. a film or droplets of liquid on the surface of the sensor. In these cases the volume outside the sensor is not homogeneously filled by the material under test, and the amount of material also determines the size of the effect.

In case the liquid forms droplets on the surface 4 of the resonator sensor these droplets will partly disturb the symmetry of the fringing field 5, in which case some of the energy in the fields in the sensor may leak into the pipe as radiation. This will not affect the resonant frequency $f_r$, but the value of the Q-factor may be slightly reduced, falsely indicating the presence of salt in the water. This can be avoided by, in a preferred embodiment of the invention, by choosing the size and the permittivity of the dielectric resonator so that the resonant frequency of the sensor is lower than the cut-off frequency of the pipe, in which case all leakage by radiation into the pipe is eliminated, as taught in the Finnish patent 69372.

Figure 7:
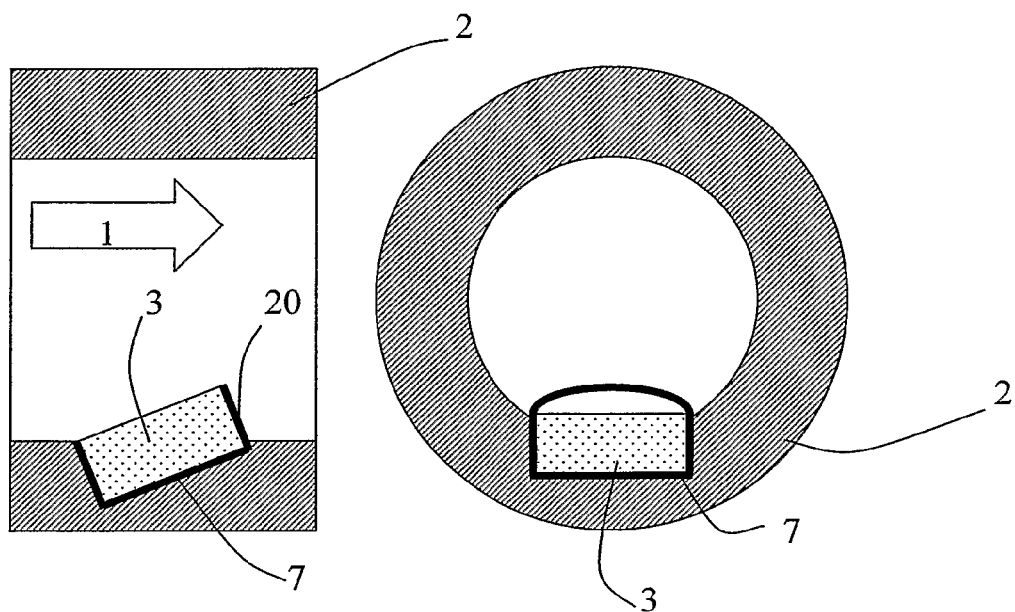
FIG. 7 shows one embodiment of a dielectric resonator sensor arrangement of the measuring instrument according to the invention.

In one alternative embodiment of the measuring instrument according to the invention the dielectric resonator sensor 3 can be arranged, preferably integrated in a wall of the pipeline 2, as illustrated in FIG. 7, in a tilted fashion with respect to a direction parallel with said pipeline 2, and with the plane surface facing the flow so that there is a step 20 on the downstream side, but no step on the upstream side. In this case the sensor is provided with a metal shield 7 so that only one of the sensor surfaces is exposed to the flow.

Figure 8:
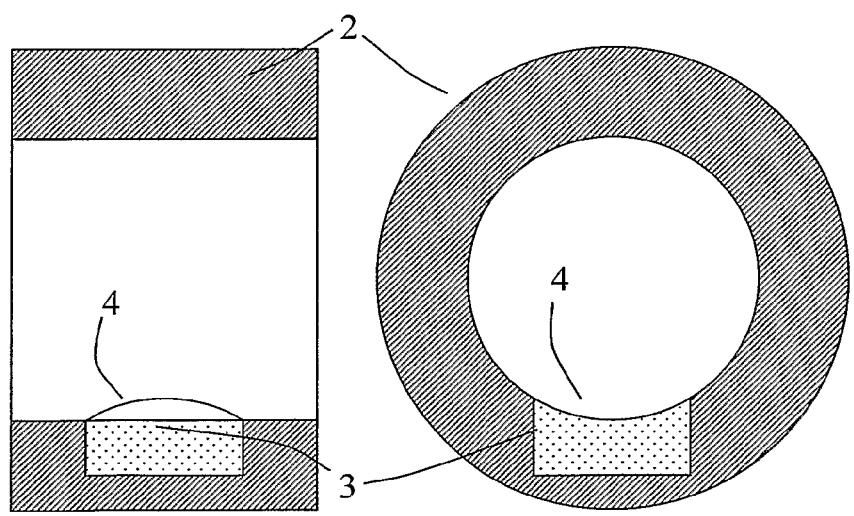
FIG. 8 shows another embodiment of a dielectric resonator sensor arrangement of the measuring instrument according to the invention.

Simulation results have shown that there is no practical difference in the performance of the sensors whether they have a plane surface or a cylindrical surface flush with the wall of the pipeline. Therefore in yet an alternative embodiment of the measuring instrument according to the invention the dielectric resonator sensor 3 can be arranged, preferably integrated in the pipeline wall, as illustrated in FIG. 8, with the surface 4 of the same cylindrical shape as the wall of pipe 2, such that the surface 4 is perfectly flush with the wall of pipe 2.

Figure 9:
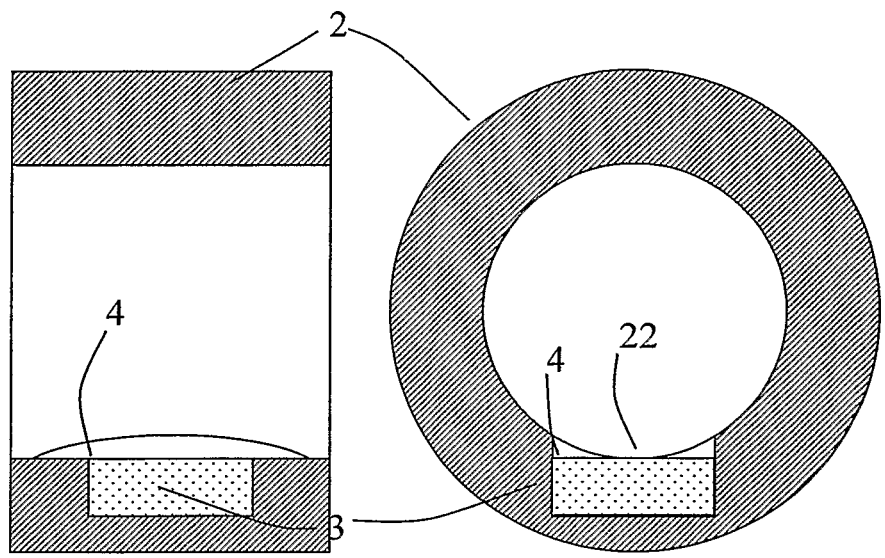
FIG. 9 shows yet an embodiment of a dielectric resonator sensor arrangement of the measuring instrument according to the invention.
Figure 10:
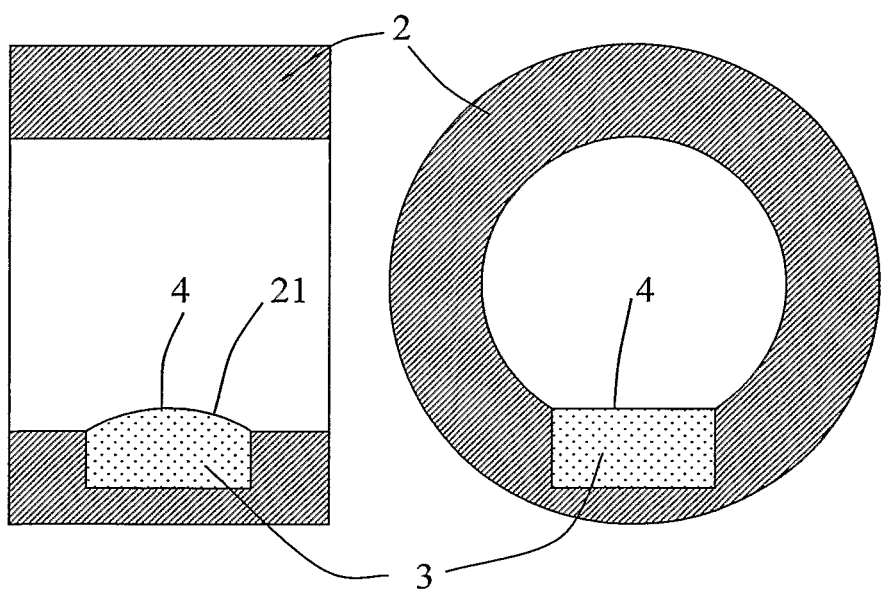
FIG. 10 shows yet an embodiment of a dielectric resonator sensor arrangement of the measuring instrument according to the invention.

In still another alternative embodiment of the measuring instrument according to the present invention the dielectric resonator sensor 3 can be integrated in the pipe wall, as illustrated in FIG. 9, so that the sensor is non-intrusive, having small cavities 22 at the edges not following the pipe wall, to form a transition from the cylindrical pipe to the plane surface of the sensor. In FIG. 10 the sensor surface 4 protrudes slightly into the flow with a curved surface 21 in the flow direction.

In another preferred embodiment of the invention illustrated in FIG. 2 at least two sensors 3 may be mounted in the pipe wall 2 so that the other is a small distance upstream of the other one. Then the sensors will see the same variations in the liquid flow at the wall, but so that the downstream sensor will see them with a short delay compared to the upstream sensor. By x-correlating the time series of the measurements from the two sensors this time delay can be found. When the distance between the two sensors is also known, the flow speed of the liquid at the wall can be found as the ratio between the distance divided by the time delay. If the average flow speed of the total flow is also known from e.g. a measurement of differential pressure over a restriction, as taught in U.S. Pat. No. 6,915,707, one can get information on the slip, i.e. the difference in speed between the liquid phase and the gas phase in the flow.

Figure 3:
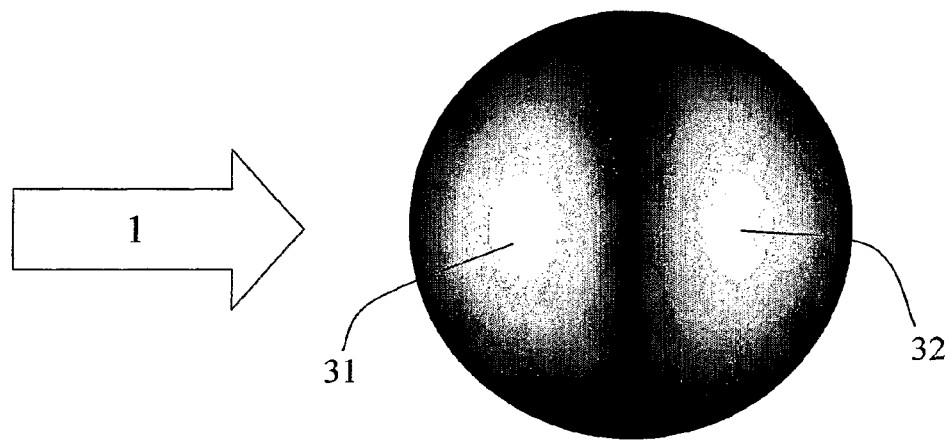
FIG. 3 illustrates the electric field strength of the $TM_{11}$ mode for flow speed measurements using the autocorrelation technique.

In an alternative preferred embodiment of the invention a single sensor with two field maxima is used for liquid flow speed measurement. E.g. the mode $TM_{11}$ in a cylindrical sensor as illustrated in FIG. 3, has two field maxima 31,32, one close to one side and another close to the opposite side, with zero electric field at the centre. When a water droplet moves over the sensor it will affect the frequency first, when it moves over one field maximum and later, when it moves over the other field maximum. The response as a function of time will therefore display two peaks. The distance between the peaks is dependent on the distance between the field maxima and the flow speed. By auto-correlating the signal the flow speed can be found. As an example a sensor, which has a permittivity of 10, a diameter of 40 mm, and a cylindrical surface flush with the pipe wall, was simulated to have a resonant frequency of 2283 MHz for $TM_{01}$, and 3200 MHz for $MT_{11}$.

In a rectangular sensor one could use the mode $TM_{21}$, which has one field maximum in each half of the cross section. In the case of sensors with two field maxima the field is not circularly symmetric, and therefore not intrinsically non-radiating. It is then important that the resonant frequency is chosen to be below the cut-off frequency of the pipe to achieve a high Q-factor.

Figure 4:
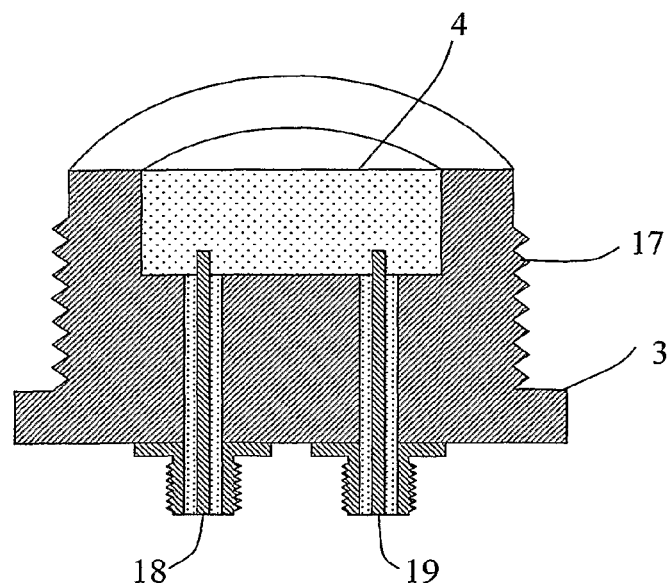
FIG. 4 illustrates a cross section of the sensor used according to the invention.

In FIG. 4 a preferred embodiment of the resonator 3 is illustrated being adapted to be screwed into the pipe wall or measuring device. The surface in this example is curved as discussed in relation to FIG. 8, but other surfaces as shown in FIGS. 7 and 9 may also be used depending on the intended use. Regarding the tilted version shown in FIG. 7 this embodiment also incorporates the metal shield 7 as the sensor housing 17 is made from metal. In FIG. 4 the coupling means to the coaxial cables connected to the measuring instrument 9 is also shown, one for the application of the signal and one for sensing the resonance. The central material 4 of the sensor is preferably made from a dielectric material having the desired electrical, mechanical and chemical properties. It must be mechanically robust enough to stand the mechanical requirements specific for the application, and it must be chemically resistant to the fluids flowing in the pipe. It must also have a permittivity that in combination with the size gives a desired resonant frequency, as described below. Suitable materials may be e.g. various ceramics like alumina ($Al_2O_3$), which has a permittivity of 10, or zirconia ($ZrO_2$), which has a permittivity of 35. Barium titanate or titanium dioxide, both with a permittivity of roughly 100, may also be used. In addition various plastic materials may in some cases be acceptable, like e.g. PEEK, which has a permittivity of 3.25.

Figure 5:
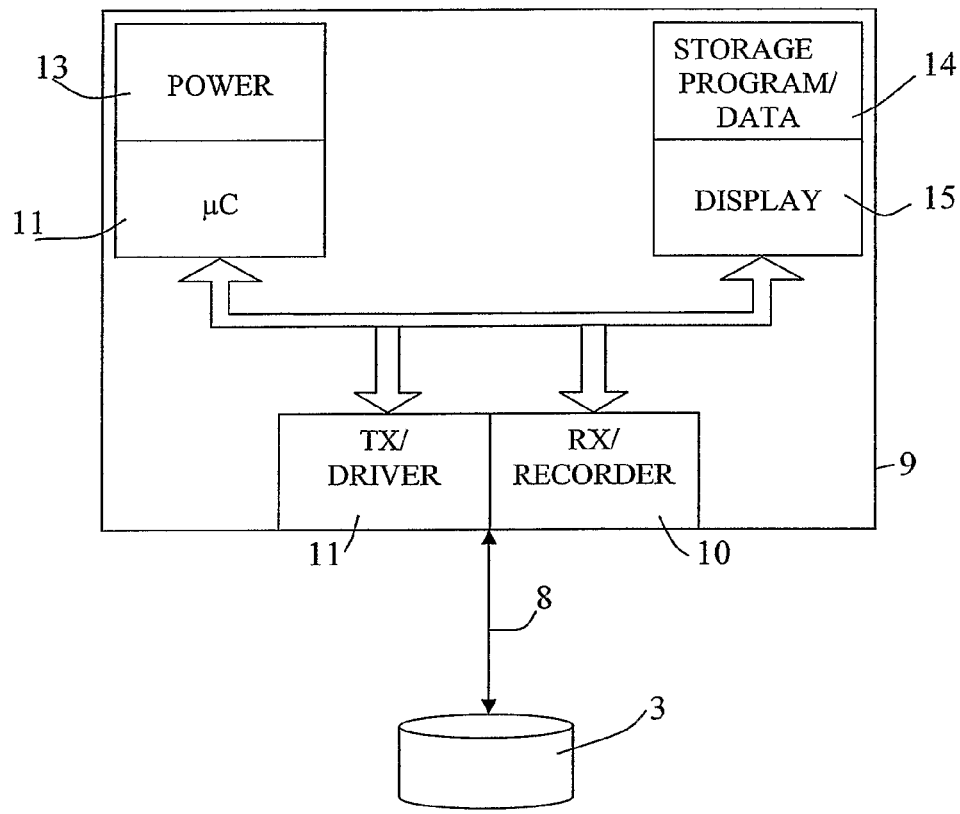
FIG. 5 illustrates the main components of a measuring instrument according to the invention including a dielectric resonator sensor arranged in a pipeline for a wet gas flow.
Figure 14:
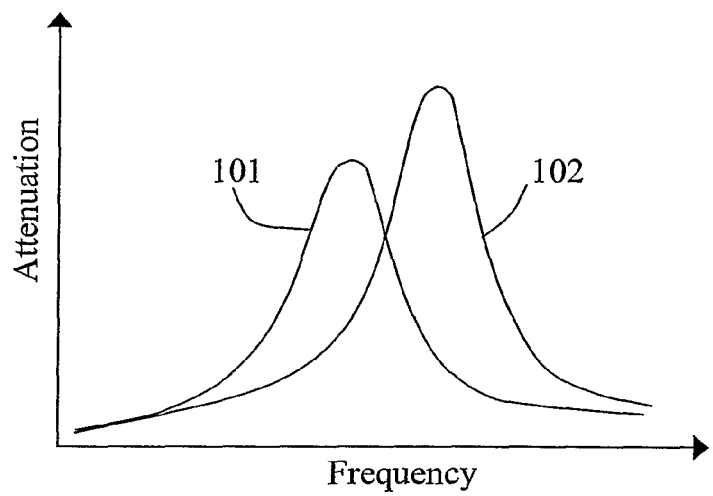
FIG. 14 illustrates measurement of the frequency response for the determination of the resonant frequency and/or quality factor in a fluid at two different water contents.
Figure 15:
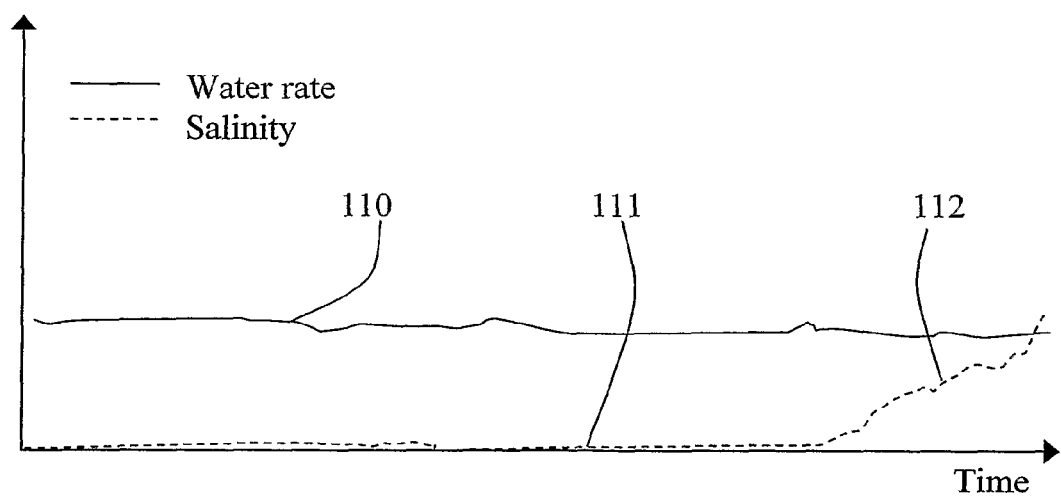
FIG. 15 illustrates a resulting curve illustrating the development of water and salinity levels in a fluid flow with time, where salinity increases towards the end, indicating presence of formation water in the process flow.

The resonant frequency $f_r$ and the Q-factor can be measured using any known method of measuring resonator sensors. One typical method illustrated in FIG. 5 is by using a sensor drive unit 9 comprising an electrical power source 13, which supplies electric power to the microwave transmitter 10, the microwave receiver 12, and the controlling microprocessor 11. The microwave transmitter 10 and receiver 12 couple the microwave signals to the resonator sensor 3 through coupling probes 8, which would typically consist of the centre conductor of the coaxial feeding cable extending a short distance into the sensor 3, thereby acting as small antennas. The microprocessor controls the transmitter to perform a frequency sweep, and records the signal from the receiver. The response would typically look like graphs 101 or 102 in FIG. 14. From such a response the microprocessor calculates the resonant frequency $f_r$ and the Q-factor using some standard technique, as e.g. U.S. Pat. No. 6,915,707 with reference to section 3.5 in the thesis by the present inventor, E. Nyfors, "Cylindrical microwave resonator sensors for measuring materials under flow", Thesis, Helsinki Univ. of Tech., Radio Lab, Report S243, May 2000, 181 p. The electronics unit may further comprice standard means for recording and displaying the measurement results as instantaneous values, or as time series as shown in FIG. 15, whatever is preferable for the application.

Figure 6:
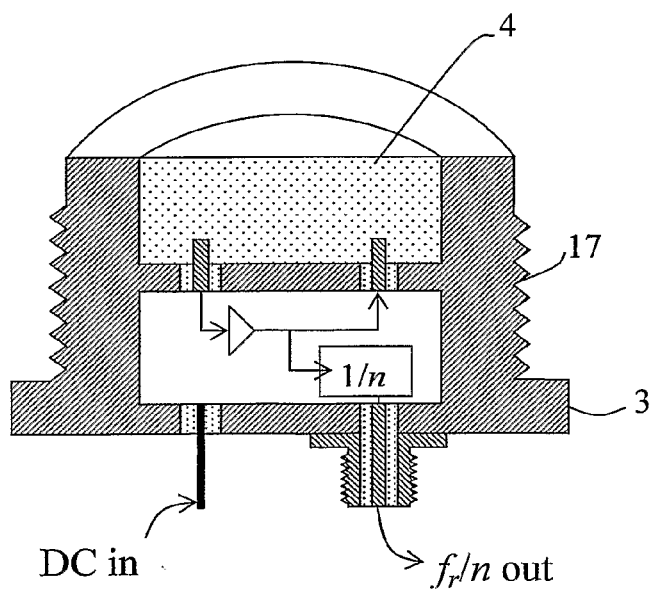
FIG. 6 illustrates a cross section of the sensor used according to the invention, with a self-oscillating electronics unit integrated behind the ceramic resonator.

In an alternative embodiment of the invention the resonant frequency of the sensor is measured by locking an oscillator to the resonance of the sensor. The oscillator may be an amplifier with positive feedback through the sensor. This method only requires very simple high-frequency electronics, which can therefore be integrated in the sensor as shown in FIG. 6. This method of measuring the resonant frequency has been described in U.S. Pat. No. 6,466,035. The difference is that in the current case the cables between the amplifier and the sensor are so short that the oscillation frequency will not jump in steps, when the resonant frequency changes, but stay locked all the time. To be able to measure the Q-factor, a phase modulator can be coupled in series with the amplifier. The frequency change caused by a certain phase modulation is proportional to the peak width of the resonance, and hence also gives information on the Q-factor. The electronics integrated in the sensor may also comprise a prescaler that reduces the frequency so much that the signal can easily be transported in a cable to a safe area, e.g. a control room, in case the sensor is located in en explosion risk zone, as most oil installations are. Alternatively an integrated frequency counter can be used, in which case the frequency information is transported as a digital signal. A further alternative is to integrate a small microcontroller to count the frequency, drive the phase modulator, and e.g. read a small integrated temperature sensor. The amount of electronics integrated in the sensor is in all these cases so small that it is possible to realize it in accordance with the regulations for intrinsically safe equipment in explosion risk zones. In this case the material and manufacturing cost can be kept low. The device will then consist of two units; the high frequency unit integrated in the sensor, and a control unit in a safe area a distance away, where the calculations are performed, and which interfaces to the users system either electronically or through a display.

In an alternative embodiment of the invention the resonant frequency $f_r$ and the Q-factor of the sensor(s) 3 are measured by the electronics unit of a wet gas meter comprising a microwave resonator sensor, as taught in U.S. Pat. No. 6,915,707. In this case no other extra electronics is needed, when the sensor(s) 3 is integrated into the wet gas meter, than microwave switches for alternatingly coupling the electronics to the microwave resonator of the wet gas meter and to sensor 3. The invention is therefore extra well suited for use as an integrated part in a microwave resonator based wet gas meter.

Figure 11:
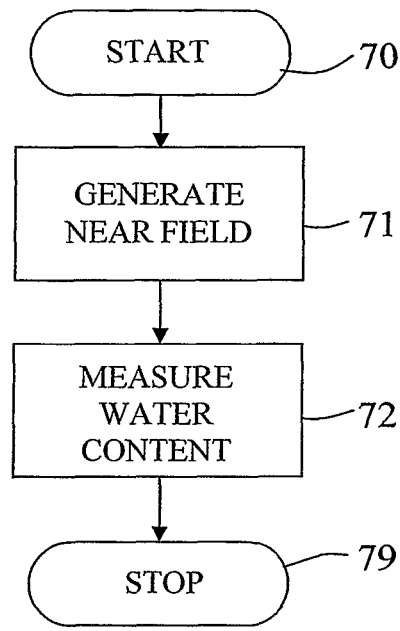
FIG. 11 is a basic flowchart of one embodiment of a method according to the invention for obtaining a measure of water content of a fluid flow in a pipeline.
Figure 12:
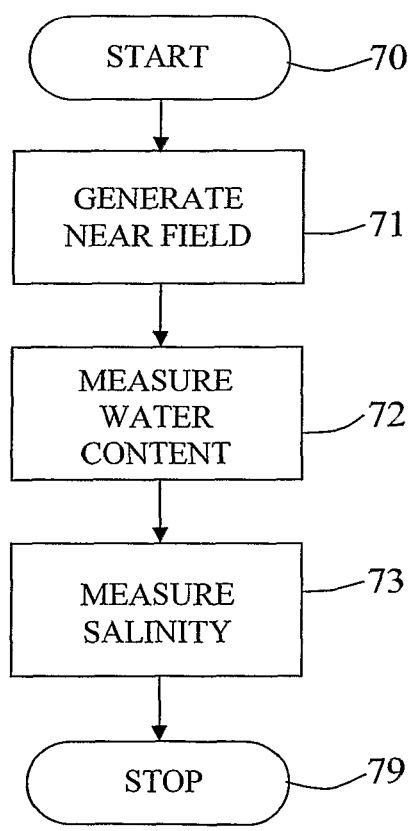
FIG. 12 is a basic flowchart of a further embodiment of a method according to the invention for obtaining a measure of water content of a fluid flow in a pipeline.

As described above the resonance recording unit 9 in FIG. 5 is coupled to the dielectric resonator sensor 3 and is adapted to record an analog or digital representation of a resonance signal, possibly also calculating the resonant frequency $f_r$ as well as the Q-factor of the dielectric resonator sensor based on recordings at multiple signal frequencies and at multiple points in time in order to generate a time-dependent array of values for the resonant frequency $f_r$ as well as the Q-factor, where the time-dependence thus also will reflect any changes in the dielectric properties in a fluid flowing in the pipeline, provided the changes are of sufficient duration and magnitude to be recordable. Thus according to one embodiment of the invention illustrated in FIG. 11 the measuring procedure is to start the equipment 70, generate the near field at the sensor(s) 71 and measure the water content from the measured resonance frequency 72, and as illustrated in FIG. 12 the salinity measurements 73 may then be measured.

Figure 13:
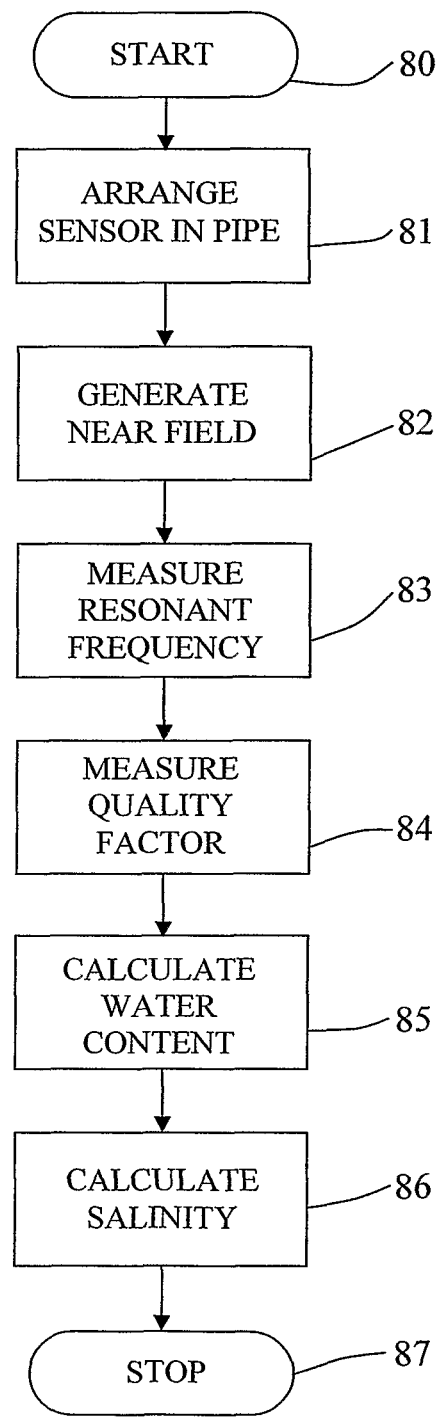
FIG. 13 is a basic flowchart of yet an embodiment of a method according to the invention for obtaining a measure of water content of a fluid flow in a pipeline.

The processing unit 11 in the recording unit 9 receives said time series of measurement values from the measuring unit. The times series could in one embodiment of the invention illustrated in FIG. 13 be values calculated in the measurement unit 9 of the resonant frequencies $f_r$ and Q-factors of the resonant properties of the dielectric resonator sensor as these properties are affected over by a fluid flow in the pipeline. In this alternative the time series could be a set of measurement values which are transmitted without further processing from the measurement unit 9 to the processing unit 11, whereby the processing unit 11 is adapted to calculate the resonant frequencies and Q-factors of the resonant properties of the dielectric resonator sensor. Thus the procedure after starting the measuring sequence 80,81 the near field is generated 82, the resonance frequency and the quality factor are measured 83,84 and used for calculating water 85, content and salinity 86. In yet another alternative the processing of measurement values could be performed, either in the measuring unit 9 or in the processing unit 11 or alternatively partly in both of these units, so as to directly generate values representing the dielectric properties of the fluid flowing in the pipeline In a wet gas flow which flows undisturbed the most of the liquid will travel as a film on the pipe wall under a large range of conditions. Thus, by arranging and using a surface sensitive dielectric resonator sensor as described in the present disclosure, a higher sensitivity to liquid content is possible, when measuring the amount and/or composition of the fluid (water/oil/condensate mixture). The surface sensitive sensor integrated in the pipe wall may in some embodiments of the invention be combined with a sensor that measures over the whole cross section of the pipeline, for example as described in the abovementioned International Patent Application PCT/NO01/00200, or U.S. Pat. No. 6,915,707. Combining these two measurements in a wet gas meter would improve the sensitivity and accuracy as compared with the known prior art techniques. In a preferable embodiment of such a combination the surface sensitive sensor is preferably placed upstream of a V-cone, where the flow typically will be substantially undisturbed.

In cases where the water volume fraction in a wet gas flow is low the water condenses from water vapor. In these cases the water is fresh water. Underneath the gas and oil in a hydrocarbon reservoir, however, there is usually water, so called formation water, which usually contains salts. If the well starts to produce this formation water, bringing salt water into the production flow, it will be highly desirable for the operators to become aware of the presence and amount of formation water as early as possible, and preferably while the levels still are fairly low, in order to give as good as possible an estimate of the total amount of salt flowing through the pipeline, primarily in order to prevent excessive corrosion of the inside surfaces of the pipeline by the salt water, or the formation of scale.

Because of the very low liquid volume fraction in the flow, an estimation of the water content and the salt content in the flow is rather difficult with wet gas meters that measure over the whole cross section of the flow.

In such a situation a meter based on a surface sensitive resonator sensor according to the present invention will provide a higher sensitivity and thereby a lower detection limit because of the formation of a liquid film on the surface of the sensor.

Figure 16:
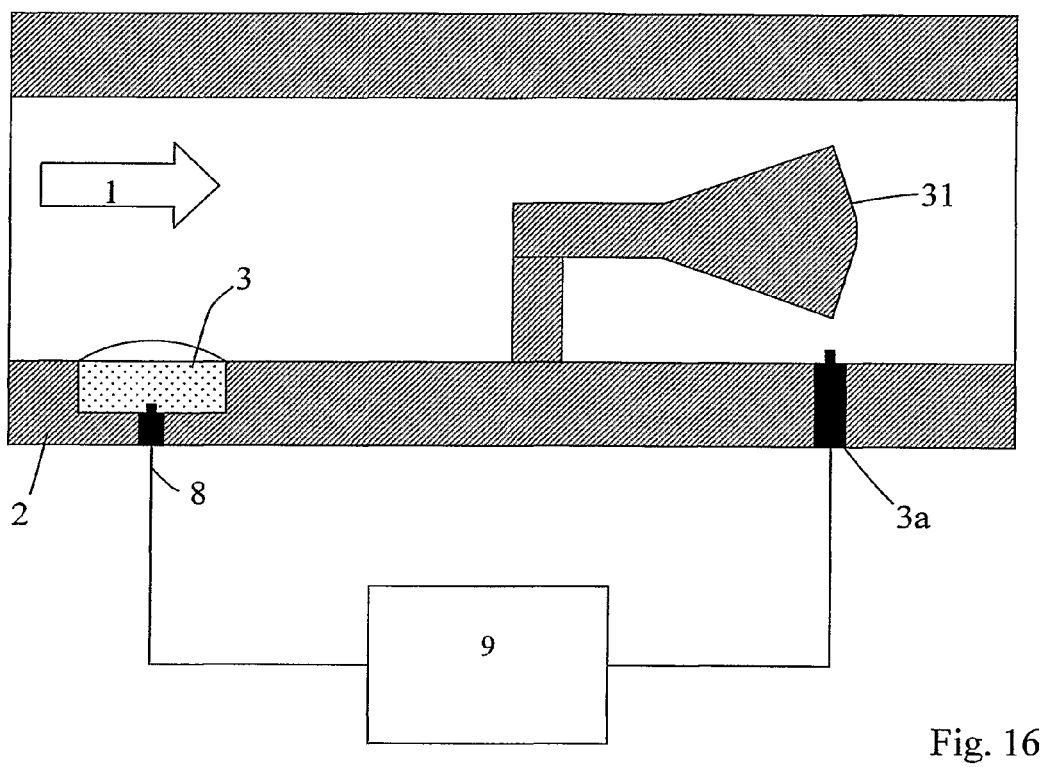
FIG. 16 illustrates an embodiment combined with a restriction on the pipe.

Some embodiments of a sensor according to the invention are used as stand-alone formation water detectors, while other embodiments of a sensor according to the invention can be combined with a conventional wet gas meter. Preferably, the surface sensitive resonator sensor is arranged upstream of flow mixing elements and/or cross-sectional differential pressure generating structures, such as e.g. a V-cone as illustrated in FIG. 16 wherein the sensor 3 is positioned upstream from the V-cone 16 and an additional sensor 3a, is positioned at the venturi. This additional sensor 3a may be a wet gas meter using the same microwave technology as the dielectric sensor.

Figure 17:
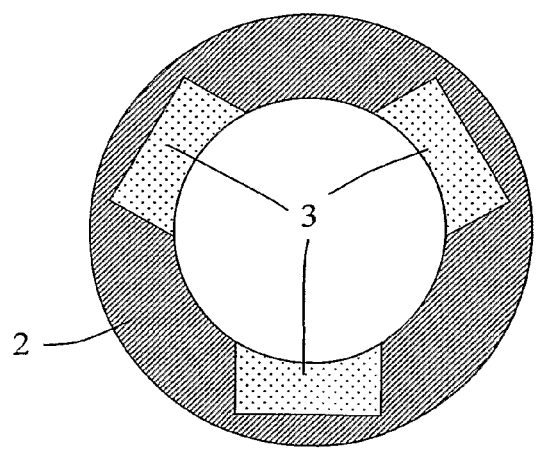
FIG. 17 illustrates an embodiment using three sensors positioned along the inner circumference of the pipe.

FIG. 17 illustrates a combination of three sensors e.g. for providing a possibility to detect asymmetric flow, for example after a bend in the pipe. Other combinations of several sensors may also be contemplated over the circumference and/or longitudinal direction of the pipe, so as to detect developments in the flow or, as stated above, for correlation measurements to find flow velocity.

Figure 18:
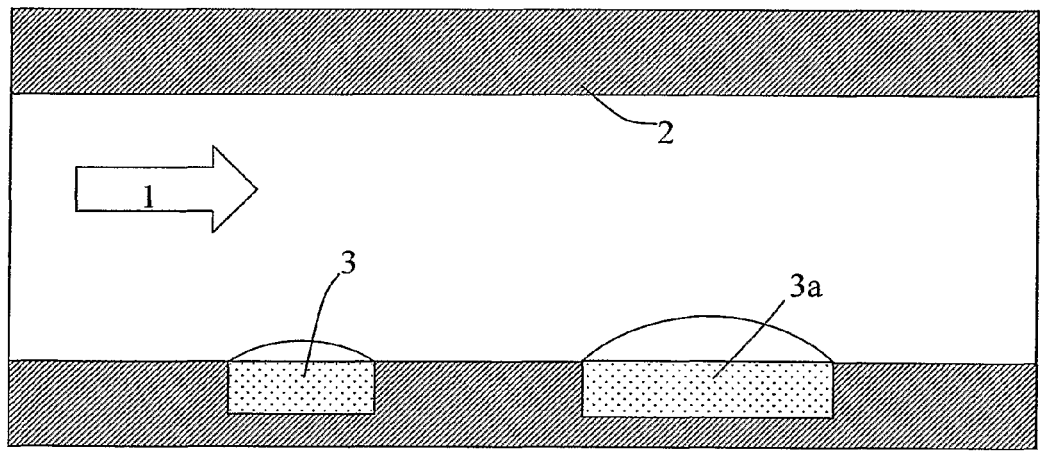
FIG. 18 illustrates an embodiment of the invention using two sensors having different sizes.

In FIG. 18 two sensor sizes are used providing different measuring depths into the flow and also measuring at different frequencies. If the flow is a combination of different fluids with differently frequency-dependent permittivities it is possible to get information about the ratio between them by measuring at two different frequencies. The sensors shown are positioned at a distance from one another in the longitudinal direction of the pipe, but in a symmetric flow the same may be achieved by positioning them in the same circumference of the pipe as illustrated in FIG. 17. The configuration illustrated in FIG. 17, comprising several sensors in the same cross section of the pipe may also be used to detect asymmetric flow, e.g. in a horizontal pipe.

Thus the surface sensitive resonator sensor provides improved measurement of the liquid content, while also improving on the formation water detection sensitivity.

The surface sensitive sensor according to the invention may in some embodiments of the invention be arranged for use as a stand-alone wet gas composition meter, while in combination with a differential pressure flow sensor (venture, orifice, V-cone, etc.) simple wet gas meter constructions yielding both composition and flow rates are possible.

Two dielectric sensors according to the invention may be mounted in the pipe for using x-correlation techniques to find the flow speed of the liquid at the wall, thereby providing information for a wet gas meter to measure the slip, i.e. the difference in flow speed between the liquid and the gas, when combined with the average speed (i.e. mainly the gas speed) measurement from the differential pressure sensor. Alternatively one sensor with two field maxima may be used and the signal auto-correlated.

The surface sensitive sensor according to the invention may also be used in cases where the liquid fraction is higher than in a typical wet gas flow, e.g. in a multiphase flow. In these cases the sensor provides an additional measurement, making it possible to derive yet another variable in a measurement, for example the salinity of the water.

Small droplets on the front surface of the sensor disturb the symmetry of the surface sensor, thereby causing it to radiate. This may be prevented by choosing frequencies so that the resonant frequency of the surface sensitive sensor is lower than the cut-off frequency of the pipe. In an example a pipe of diameter $D_p$=74.6 mm has a cut-off frequency of $f_c$=2357 MHz. It is inversely proportional to the diameter, i.e. when $D_p$ is doubled, $f_c$ is halved. A surface sensor of diameter $D_s$=40 mm and permittivity of $\in_d$=10 has a resonant frequency of $f_c$=2285 MHz and with a permittivity of 77 the resonant frequency is 838 MHz. The resonant frequency is approximately inversely proportional to both the diameter and the square root of the permittivity:

$$f_r \propto \frac{1}{D_s \sqrt{\varepsilon_d}}$$

The height of the dielectric cylinder is not very critical, and it does not have any strong influence on the resonant frequency, but a preferred value would typically be in the range 0.3-0.5 times the diameter. When the sensor does not radiate even with water droplets on the surface due to the cut-off frequency of the pipe, only the absorption of microwaves by the medium under test (MUT) affects the Q-factor, in which case the surface sensor can be used as a formation water detector, or salinity detector. When no other variables in the flow affect the Q-factor than the absorption caused by the salt content of the formation water, and the surface sensitive sensor according to the invention measures on a higher concentration of liquid on the wall than the wet gas meter measuring over the whole cross section of the pipe, a significant improvement in the formation water detection can be achieved. Therefore the start of the production of formation water can be detected much earlier, thereby significantly reducing the effects of the salt production, when actions to control the oil well can be taken earlier. The sensor also improves the measurement of small values of WVF because the sensor measures primarily the liquid on the pipe wall, and is far less affected by the variations in the gas temperature and pressure than a conventional wet gas meter.

Figure 19:
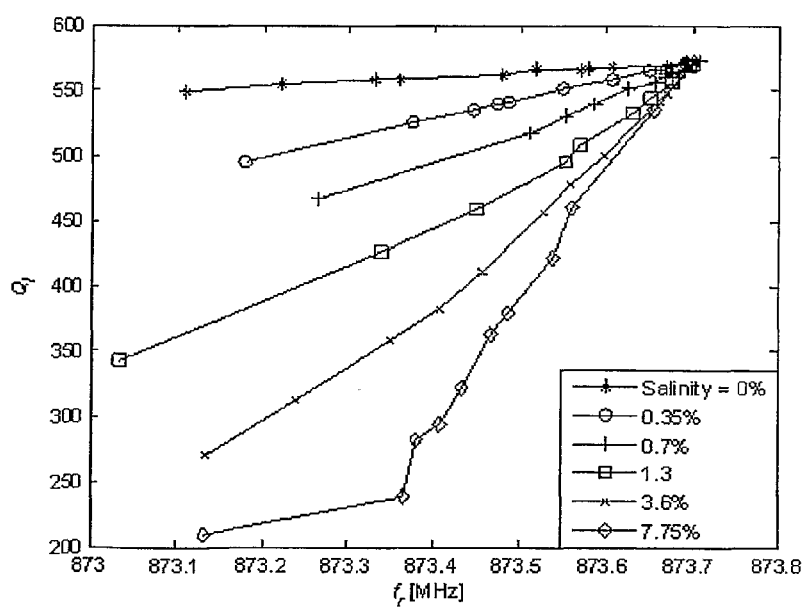
FIG. 19 illustrates measurements performed with different salinities in the flow.

Laboratory tests have shown that a sensor according to the invention can detect and measure the salt content in very small amounts of water indeed. FIG. 19 shows graphs measured with a sensor in the laboratory. The sensor is 40 mm in diameter, and it has a permittivity of 77. The measurements were performed by spraying a small number of very small water droplets of varying salinity on the surface 4 of the sensors. From the graphs it is clear that a combined measurement of resonant frequency and Q-factor can be used to calculate the salinity, while a measurement of the Q-factor alone can be used to detect the presence of salt in the water. To be able to calculate the amount of water from the measurements the sensor must be empirically calibrated against a reference in a test loop. This is because the formation of a liquid film and droplets is different under flowing conditions and static laboratory conditions.

In cases where there is little or no gas the resonance of the surface sensitive sensor according to the invention may be completely lost if the liquid flowing in the pipeline is water-continuous and the water contains salt, due to the strong absorption. By measuring the shape of the frequency response and detecting changes in this shape, changes in the composition of the fluid flow may be recorded, even though no resonance is distinguished in the response. Such a measurement is made by measuring the insertion loss (i.e. the attenuation through the sensor) in a frequency range, e.g. an octave, and by applying otherwise known processing methods for shape recognition on the response, or extraction of parameters, using e.g. multivariate analysis or neural networks. In such a way it is possible to estimate the composition of the flow.

Thus the invention relates to improvements in water and possibly salinity measurements in a wet gas system. The invention incorporates a dielectric resonator for use at high frequencies being mounted in the pipe wall and being in contact with the flow in the pipe. The sensor has one end facing the pipe interior with a preferably symmetrical electrical field extending into the flow close to the wall. The permittivity of the flow through which the field extends thus affects the resonance frequency and quality factor of the sensor, which may be measured through probes coupled to suitable measuring instruments Different resonance modes may be measured, where the resonance mode with cylindrical symmetry is virtually non-radiating. The resonant frequency is preferably below the cut-off of the pipe to be completely non-radiating even when droplets on the surface disturb the symmetry. Different embodiments may be used, e.g. having a plane surface facing the flow, tilted without step on upstream side, or retracted to be flush with wall along centre line and "cavities" in pipe wall to avoid steps, or mounted sticking into the pipe to be flush with wall at the rim normal to the centre line and with ramps upstream and downstream in the centre to avoid steps. The sensor may also have a cylindrical surface facing the flow completely flush with the pipe wall.

The system according to the invention may also be implemented on the surface of a body mounted inside the pipe (e.g. V-Cone, cylindrical "torpedo") and the sensor may be used to measure the water content of the fluid on the wall in a wet gas flow, possibly as an additional sensor in a wet gas meter to improve the water measurement, or as a stand alone sensor.

By combining the resonant frequency and quality factor both the amount of water and condensate/oil in the liquid at the wall may be measured or just the resonant frequency may be used to measure the amount of water. The quality factor may be used to detect conductivity, i.e. the presence of salt, e.g. from formation water, and thus act as a salinity detector used as an additional sensor in a wet gas meter to improve the sensitivity of the formation water detection by measuring on the wall, where the concentration of water is higher than in the cross section of the flow.

As discussed above at least two sensors mounted upstream and downstream of each other may be used for measuring the flow speed of the liquid on the wall by x-correlation. Thus they are used as additional sensors in a wet gas meter, thereby making possible the calculation of the slip, i.e. the speed difference between the gas and the liquid phases.

If used in a water-continuous multiphase flow, or with a conducting water film, causing so high attenuation that the resonance disappears, then measuring the frequency response over a broad bandwidth, curve-fitting to find out the complex dielectric constant of the flow, and hence the water content and/or salinity.

The invention also relates to a method of improving the water content measurement sensitivity in a wet gas meter by adding such a sensor measuring on the wall, where the concentration of liquid is higher than in the middle of the pipe. This would improve the formation water detection sensitivity of a wet gas meter by adding such a sensor measuring on the wall, where the concentration of water is higher. This could be used for measuring the slip with a wet gas meter by adding at least two such sensors measuring the speed of the liquid on the wall by x-correlation.

To summarize the main aspect of the invention it involves a measuring instrument for measuring water content or other properties of a fluid flow 1 in a pipeline 2 for transporting fluid hydrocarbon, especially a multiphase or wet gas flow. The instrument utilizes at least one dielectric resonator sensor 3 adapted for forming a time varying electric field extending from said resonator sensor (3). The frequency applied to the sensor is usually in the microwave range but other frequency ranges ay also be applied depending on the pipe dimensions and the permittivity of the flow. The electric field extends mainly into an inner volume section adjacent or close to the inside wall of said pipeline. The instrument further comprises a measuring unit 9 adapted for measuring a resonance frequency of said resonator sensor 3, which depends upon the flow content, and estimate chosen characteristics of a fluid flow in said pipeline (2) based on said measurement of a resonance frequency.

The invention claimed is:

1. A measuring instrument for measuring water content in a fluid flow in a pipeline for transporting fluid hydrocarbon, the measuring instrument comprising:
   at least one dielectric resonator sensor configured to form a time varying electric field extending from said resonator sensor, the time varying electric field extending into an inner volume section adjacent an inside wall of said pipeline, wherein the resonator sensor is seated in or against the inside wall and the resonator sensor faces a region of the inside wall devoid of the resonator sensor, and
   a measuring unit configured to measure a resonance frequency of said resonator sensor and estimate a water content of a fluid flow in said inner volume section adjacent an inside wall of said pipeline based on said measurement of a resonance frequency.

2. The measuring instrument according to claim 1, wherein said time varying electric field comprises a frequency component corresponding to a $TM_{01}$ mode of the resonator sensor.

3. The measuring instrument according to claim 1, wherein said time varying electric field comprises a frequency component corresponding to a $TM_{11}$ mode of the resonator sensor.

4. The measuring instrument according to claim 3, wherein said resonator sensor is oriented relative to a flow direction of the fluid flow so as to produce the two resulting field maxima along the flow direction so that fluids passing the field maxima will affect the fields at the two maxima at different times, and wherein the measuring unit comprises means for measuring the variations in the resonance frequency in time and calculate the flow velocity from an autocorrelation of a time series of said measurements.

5. The measuring instrument according to claim 1 wherein the sensor includes a surface flush with an inner surface of the pipeline.

6. A measurement instrument for measuring water content in a fluid flow in a pipeline for transporting fluid hydrocarbon, the measuring instrument comprising:
   at least one dielectric resonator sensor configured to project a time varying electric field extending from said resonator sensor into an inner volume of the pipeline, wherein said resonator sensor is tilted with respect to a direction parallel with said pipeline, and the resonator sensor includes a plane surface facing the fluid flow, and
   a measuring unit configured to measure a resonance frequency of said resonator sensor and estimate a water content of a fluid flow through said inner volume of said pipeline based on said measurement of a resonance frequency.

7. The measurement instrument according to claim 1, wherein said resonator sensor includes a plane surface substantially perpendicular to a cross sectional radius of the pipeline, and the plane surface forms a ramp in at least one of an upstream direction and a downstream direction of the flow.

8. The measurement instrument according to claim 1, wherein said measuring unit is adapted for obtaining a measurement of the quality factor of said resonator sensor.

9. The measurement instrument according to claim 1, wherein the resonator sensor includes an oscillator locked to a resonance frequency of the resonator sensor, the resonance frequency being measured by measuring an oscillation frequency, the oscillator being constituted by a phase modulator coupled in series with an amplifier between terminal electrodes in the resonator sensor.

10. The measurement instrument according to claim 9, wherein a Q-factor of the resonance is measured as a function of the frequency change caused by a phase change applied to the resonator sensor.

11. The measuring instrument according to claim 6 wherein said time varying electric field comprises a frequency component corresponding to a $TM_{01}$ mode of the resonator sensor.

12. The measuring instrument according to claim 6, wherein said time varying electric field comprises a frequency component corresponding to a $TM_{11}$ mode of the resonator sensor.

13. The measuring instrument according to claim 12 wherein said resonator sensor is oriented relative to the direction of the fluid flow so as to produce the two resulting field maxima along the flow direction so that fluids passing the field maxima will affect the fields at the two maxima at different times, and wherein the measuring unit comprises means for measuring the variations in the resonance frequency in time and calculate the flow velocity from an autocorrelation of a time series of said measurements.

14. The measuring instrument according to claim 6 wherein the sensor includes a surface flush with an inner surface of the pipeline.

15. The measurement instrument according to claim 6 wherein said resonator sensor includes a plane surface substantially perpendicular to a cross sectional radius of the pipeline, and the plane surface forms a ramp in at least one of an upstream direction and a downstream direction of the flow.

16. The measurement instrument according to claim 6 wherein said measuring unit is adapted for obtaining a measurement of the quality factor of said resonator sensor.

17. The measurement instrument according to claim 6 wherein the resonator sensor includes an oscillator locked to a resonance frequency of the resonator sensor, the resonance frequency being measured by measuring an oscillation frequency, the oscillator being constituted by a phase modulator coupled in series with an amplifier between terminal electrodes in the resonator sensor.

18. The measurement instrument according to claim 17 wherein a Q-factor of the resonance is measured as a function of the frequency change caused by a phase change applied to the resonator sensor.

19. A measuring instrument to determine a liquid content in a fluid flowing through a pipe, the measuring instrument comprising:
- a dielectric resonator having a resonating surface adjacent an interior wall of the pipe, wherein a cross-section of the interior wall at the resonator resonating surface includes portions of the wall devoid of the resonating surface and wherein the resonator is configured to project a time varying electric fringing field extending into a flow of the fluid through the pipe and the resonator is configured to generate a signal indicative of a resonance of the resonating surface in response to the fringing field, and
- a measuring unit configured to measure a resonance frequency of resonating surface based on the signal generated by the resonator and calculate a content of a liquid in the fluid flowing through the pipe based on the resonance frequency.

* * * * *